US011253450B2

(12) United States Patent
Lane

(10) Patent No.: US 11,253,450 B2
(45) Date of Patent: Feb. 22, 2022

(54) SCALP CARE COMPOSITION WITH IMPROVED STABILITY

(71) Applicant: The Procter & Gamble Company, Cincinnati, OH (US)

(72) Inventor: Brandon Scott Lane, Hamilton, OH (US)

(*) Notice: Subject to any disclaimer, the term of this patent is extended or adjusted under 35 U.S.C. 154(b) by 0 days.

(21) Appl. No.: 16/720,345

(22) Filed: Dec. 19, 2019

(65) Prior Publication Data

US 2020/0214953 A1 Jul. 9, 2020

Related U.S. Application Data

(60) Provisional application No. 62/782,634, filed on Dec. 20, 2018.

(51) Int. Cl.
| | |
|---|---|
| A61K 8/27 | (2006.01) |
| A61K 8/34 | (2006.01) |
| A61K 8/42 | (2006.01) |
| A61K 8/49 | (2006.01) |
| A61K 8/81 | (2006.01) |
| A61K 8/891 | (2006.01) |
| A61Q 5/00 | (2006.01) |

(52) U.S. Cl.
CPC ............... *A61K 8/27* (2013.01); *A61K 8/34* (2013.01); *A61K 8/345* (2013.01); *A61K 8/42* (2013.01); *A61K 8/4926* (2013.01); *A61K 8/4953* (2013.01); *A61K 8/8176* (2013.01); *A61K 8/891* (2013.01); *A61Q 5/006* (2013.01)

(58) Field of Classification Search
None
See application file for complete search history.

(56) References Cited

U.S. PATENT DOCUMENTS

| | | | |
|---|---|---|---|
| 4,796,812 | A | 1/1989 | Grollier |
| 6,060,044 | A | 5/2000 | Cretois |
| 8,360,973 | B2 | 1/2013 | Bazin |
| 9,996,674 | B2 | 6/2018 | Segman |
| 10,543,157 | B2 | 1/2020 | Davis |
| 2002/0150287 | A1 | 10/2002 | Kobayashi |
| 2002/0183988 | A1 | 12/2002 | Skaanning |
| 2003/0008855 | A1* | 1/2003 | Simon ............... A61K 8/4933 514/184 |
| 2003/0215522 | A1 | 11/2003 | Johnson |
| 2004/0213751 | A1 | 10/2004 | Schwartz |
| 2009/0274642 | A1 | 11/2009 | Dawson, Jr. |
| 2010/0106679 | A1 | 4/2010 | Yamaguchi |
| 2012/0309733 | A1 | 12/2012 | Chang |
| 2014/0028822 | A1 | 1/2014 | Khadavi |
| 2014/0071456 | A1 | 3/2014 | Podoleanu |
| 2014/0120048 | A1 | 5/2014 | Krueger |
| 2014/0171471 | A1 | 6/2014 | Krueger |
| 2014/0378810 | A1 | 12/2014 | Davis |
| 2015/0217465 | A1 | 8/2015 | Krenik |
| 2015/0272865 | A1* | 10/2015 | Mette ............... A61K 8/731 424/94.1 |
| 2016/0038397 | A1* | 2/2016 | Markland ............. A61Q 19/10 424/70.12 |
| 2016/0310393 | A1 | 10/2016 | Chang |
| 2016/0346184 | A1 | 12/2016 | Schwartz |
| 2017/0135932 | A1 | 5/2017 | Schwartz |
| 2017/0270593 | A1 | 9/2017 | Sherman |
| 2017/0367963 | A1* | 12/2017 | Kadir ............... A61K 8/86 |
| 2018/0040052 | A1 | 2/2018 | Robinson |
| 2018/0225673 | A1 | 8/2018 | Dubey |
| 2018/0325791 | A1 | 11/2018 | Lane |
| 2019/0035149 | A1 | 1/2019 | Chen |
| 2019/0350514 | A1 | 11/2019 | Purwar |
| 2019/0350819 | A1 | 11/2019 | Hamersky |
| 2019/0350831 | A1 | 11/2019 | Schwartz |
| 2019/0355115 | A1 | 11/2019 | Niebauer |

FOREIGN PATENT DOCUMENTS

| | | |
|---|---|---|
| DE | 102012203240 A1 | 3/2013 |
| DE | 202015002188 U1 | 5/2015 |
| WO | WO9939683 A1 | 8/1999 |
| WO | WO2012058557 A2 | 5/2012 |
| WO | 2014073456 A1 | 5/2014 |
| WO | 2014208162 A1 | 12/2014 |

OTHER PUBLICATIONS

All final and non-final office actions for U.S. Appl. No. 15/976,485.
All final and non-final office actions for U.S. Appl. No. 16/412,745.
All final and non-final office actions for U.S. Appl. No. 16/441,749.
All final and non-final office actions for U.S. Appl. No. 16/413,920.
PCT International Search Report and Written Opinion for PC/US2018/032046 dated Jun. 27, 2018.
PCT International Search Report and Written Opinion for PCT/US2019/032382 dated Jul. 31, 2019.
PCT International Search Report and Written Opinion for PCT/US2019/032402 dated Aug. 28, 2019.
PCT International Search Report and Written Opinion for PCT/US2019/032404 dated Jul. 30, 2019.
Schwartz, J.R. et al., "The role of oxidative damage in poor scalp health: ramifications to causality and associated hair growth", International Journal of Cosmetic Science, vol. 37, No. Suppl. 2, Sp. Iss. SI, Dec. 2015, pp. 9-15.
"Anti-Dandruff Treatment Hair Cream", Mintel, Sep. 3, 2018.
"Balancing and Anti-Dandruff Shampoo", Mintel, Jan. 6, 2014.
"Double Care Anti-Dandruff Treatment Hair Cream", Mintel, Oct. 16, 2012.
"Hair Lotion", Mintel, Oct. 7, 2019.
"Moist-Up Eye Cream", Mintel, Nov. 11, 2009.
"Moisturizing Anti-Dandruff Shampoo", Mintel, Mar. 17, 2016.
PCT International Search Report and Written Opinion for PCT/US2019/066785 dated Mar. 26, 2020.

* cited by examiner

*Primary Examiner* — Quanglong N Truong
(74) *Attorney, Agent, or Firm* — Linda M. Sivik

(57) ABSTRACT

The present invention is directed to a scalp care composition comprising from about 1% to about 99% of an aqueous carrier; from about 0.05% to about 10% of a nonionic, water-soluble, cross-linked N-vinyl lactam homopolymers; and from about 0.001% to 10% of an insoluble zinc salt.

16 Claims, No Drawings

SCALP CARE COMPOSITION WITH IMPROVED STABILITY

FIELD OF THE INVENTION

The present invention is directed to scalp care compositions where it has been found that the addition of nonionic, water-soluble, cross-linked N-vinyl lactam homopolymers combination with an insoluble zinc salt provide an unexpected improvement in stability.

BACKGROUND OF THE INVENTION

Hair and scalp leave on treatment compositions comprising various combinations of hair and scalp actives, are known in the art and are commercially available. These compositions may have rheological properties that optimize the consumer perceived usage experience (non-dripping, spread, coverage, etc.).

Nevertheless, some consumers desire an anti-dandruff leave on treatment which provides a level of anti-dandruff efficacy that can replace other anti-dandruff rinse off products or is used in addition to rinse off anti-dandruff products or provide leave on benefits to hair and scalp that are difficult to achieve with a rinse off product. Consequently, a need exists for a treatment product that combines core anti-dandruff efficacy with additional scalp health and hair benefits that the consumer can notice and feel, i.e. effective, and is delightful to use.

Previous work in zinc pyrithione (ZPT) containing rinse-off products has shown that the inclusion of insoluble zinc salts into these systems, can provide a synergistic skin health benefit and increase the efficacy of the product beyond the levels of the singularly containing ZPT products. While this benefit has been explored heavily in the shampoo space, it has yet to be leveraged in the leave-on scalp treatments do to complexities and incompatibilities between insoluble zinc salts and the necessary rheology modifiers required to produce a stable formula. Typically, when formulating leave-on scalp treatments that contain particulate actives, the ability to suspend said actives in the formula matrix to ensure shelf stability and to prevent agglomeration of the particles in the system is necessary. As a rule, the most common of the rheology modifiers available for this purpose are not compatible with the system for one of a few reasons; presence of carboxyl groups on the anionic polymers which binds and renders the insoluble zinc salts ineffective, lack of surfactants and other hydrophobic materials necessary for non-ionic associative thickeners to build rheology, and incompatibilities with ethanol in our commonly hydro-alcoholic chassis. To achieve a physically and chemically stable system, significant efforts have been spent on identifying materials capable of meeting all of the present invention's needs from a performance, stability and efficacy standpoint. Surprisingly, there is a very limited group of materials capable of fulfilling all of these attributes. In the present invention, an effective material has been surprisingly found which is a nonionic, water-soluble, cross-linked N-vinyl lactam homopolymer. An example of such material is cross-linked N-vinyl-2-pyrrolidone homopolymer.

SUMMARY OF THE INVENTION

The present invention is directed a scalp care composition comprising from about 1% to about 99% of an aqueous carrier; from about 0.05% to about 10% of a nonionic, water-soluble, cross-linked N-vinyl lactam homopolymers; and from about 0.001% to 10% of an insoluble zinc salt.

These and other features, aspects, and advantages of the present invention will become evident to those skilled in the art from a reading of the present disclosure.

DETAILED DESCRIPTION OF THE INVENTION

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity, unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Apply" or "application," as used in reference to a composition, means to apply or spread the compositions of the present invention onto keratinous tissue such as the hair.

"Dermatologically acceptable" or "cosmetically acceptable" means that the compositions or components described are suitable for use in contact with human skin tissue without undue toxicity, incompatibility, instability, allergic response, and the like. All compositions described herein which have the purpose of being directly applied to keratinous tissue are limited to those being cosmetically acceptable.

"Safe and effective amount" means an amount of a compound or composition sufficient to significantly induce a positive benefit.

"Leave-on," in reference to compositions, means compositions intended to be applied to and allowed to remain on the keratinous tissue. These leave-on compositions are to be distinguished from compositions, which are applied to the hair and subsequently (within a few minutes or less) removed either by washing, rinsing, wiping, or the like. Leave-on compositions exclude rinse-off applications such as shampoos, rinse-off conditioners, facial cleansers, hand cleansers, body washes, or body cleansers. The leave-on compositions may be substantially free of cleansing or detersive surfactants. For example, "leave-on compositions" may be left on the keratinous tissue for at least 15 minutes. For example, leave-on compositions may comprise less than 1% detersive surfactants, less than 0.5% detersive surfactants, or 0% detersive surfactants. The compositions may, however, contain emulsifying, dispersing or other processing surfactants that are not intended to provide any significant cleansing benefits when applied topically to the hair.

"Soluble" means at least about 0.1 g of solute dissolves in 100 ml of solvent, at 25° C. and 1 atm of pressure. Insoluble zinc salt means that the zinc salt has water solubility of less than 0.1 g in 100 ml.

All ratios are weight ratios, unless specifically stated otherwise. All ranges are inclusive and combinable. The number of significant digits conveys neither a limitation on the indicated amounts nor on the accuracy of the measurements. The term "molecular weight" or "M. Wt." as used herein refers to the weight average molecular weight unless otherwise stated. The weight average molecular weight may be measured by gel permeation chromatography "QS" means sufficient quantity for 100%.

The term "substantially free from" or "substantially free of" as used herein means less than about 1%, or less than about 0.8%, or less than about 0.5%, or less than about 0.3%, or about 0%, by total weight of the composition.

"Hair," as used herein, means mammalian hair including scalp hair, facial hair and body hair, particularly on hair on the human head and scalp.

"Derivatives," as used herein, includes but is not limited to, amide, ether, ester, amino, carboxyl, acetyl, acid, salt and/or alcohol derivatives of a given compound.

"Polymer," as used herein, means a chemical formed from the polymerisation of two or more monomers. The term "polymer" as used herein shall include all materials made by the polymerisation of monomers as well as natural polymers. Polymers made from only one type of monomer are called homopolymers. A polymer comprises at least two monomers. Polymers made from two or more different types of monomers are called copolymers. The distribution of the different monomers can be calculated statistically or blockwise, both possibilities are suitable for the present invention. Except if stated otherwise, the term "polymer" used herein includes any type of polymer including homopolymers and copolymers.

I. SCALP CARE COMPOSITIONS

The scalp care composition of the present invention may include one or more solubilizing agents. Nonlimiting examples of solubilizing agent can be water miscible non-ionic surfactants, such as alkyl alkoxylate ethers, alkoxylated esters, organic acid esters or ethers of sugars or polysaccharides, glycol esters, glycerin esters and others. More specific classes that can serve as solubilizing agents are saturated or unsaturated alkyl ethoxylate ethers, ethoxylated organic acid esters (saturated or unsaturated), sorbate esters, polysorbates. Nonlimiting examples of specific materials that can serve as solubilizing agents include laureth-12, laureth-23, oleth-10, oleth-20, steareth-20, steareth-21, ceteth-20, PPG-26 Buteth-26, such as Creasoluble No. 4, PPG-1-PEG-9 lauryl glycol ether, PEG-40 hydrogenated castor oil, such as Cremaphor RH40, PEG-25 hydrogenated castor oil, yPEG-50 hydrogenated castor oil, POE-30 castor oil, POE-40 castor oil, heptyl glucoside, such as Sepiclear G7, Polysorbate-80, such as Tween 80, Polysorbate-20, Polysorbate-28, Polysorbate-60, Polysorbrate-61, Polysorbate-85, glyceryl stearate, PEG-20 stearate, PEG-40 stearate, PEG-100 stearate, PEG-8 dilaurate, sorbitan monooleate, sorbitan monolaurate, and others.

The scalp care composition may include from about 0.1% to about 5% of one or more solubilizing, agent, further from about 0.5% to about 3% of one or more solubilizing agents, and further from about 1% to about 2% of one or more solubilizing agents.

Solvents

The scalp care composition may include one or more solvents. The scalp care composition may include one or more organic solvents. Non-limiting examples may include dipropyleneglycol, propylene glycol, butylene glycol, 1,4-butanediol, 3-allyloxy-1,2-propanediol, dipropylene glycol n-butyl ether, 1,2-hexanediol, dimethyl isosorbide, ethanol, 1,3-butanediol, 1,3-propanediol, 2,2'-thiodiethanol, and 1,6-hexanediol, or combinations thereof.

The scalp composition may further include one or more additional hair growth stimulating agents, such as those disclosed in U.S. Patent Application Publication No. 2010/0120871. Accordingly, non-limiting examples of additional hair growth stimulating agents include indole compounds, xanthine compounds, vitamin $B_3$ compounds, panthenol compounds, and derivatives thereof.

Xanthine Compounds

The scalp care compositions can further include a xanthine compound. As used herein, "xanthine compound" means one or more xanthines, derivatives thereof, and mixtures thereof. Xanthine compounds that can be useful herein include, but are not limited to, caffeine, xanthine, 1-methylxanthine, theophylline, theobromine, derivatives thereof, and mixtures thereof. Accordingly, the composition may include from about 0.01% to about 10% of the xanthine compound, from about 0.5% to about 5% of the xanthine compound, or from about 1% to about 2% of the xanthine compound, for example, wherein the percentage is a weight percentage based on the total weight of the final hair care composition. For example, the hair care composition may further include about 0.75% of caffeine.

In the scalp care composition, the amount of xanthine may be decreased to lessen potential white residue the may result from various formulations when the xanthine is present in higher amounts. The scalp care composition may comprise from about 0.01% to about 1% xanthine, alternative from about 0.01% to about 0.75% xanthine, alternatively from about 0.01% to about 0.5% xanthine, alternatively from about 0.01% to about 0.25% xanthine, and alternatively from about 0.01% to about 0.1% xanthine. The scalp care composition may have no xanthine.

Vitamin $B_3$ Compounds

The scalp care compositions can further include a vitamin B3 compound. As used herein, "vitamin $B_3$ compound" means nicotinic acid, niacinamide, nicotinyl alcohol, derivatives thereof, and mixtures thereof. The vitamin $B_3$ compound may be included as the substantially pure material, or as an extract obtained by suitable physical and/or chemical isolation from natural (e.g., plant) sources. The scalp composition may include from about 0.1% to about 25% of the vitamin $B_3$ compound; from about 0.1% to about 15% of the vitamin $B_3$ compound; from about 0.1% to about 7.5%, from about 3.5% to about 7.5% of the vitamin $B_3$ compound, for example, wherein the percentage is a weight percentage based on the total weight of the final hair care composition. The scalp care composition may further include about 2.5% of vitamin $B_3$.

Panthenol Compounds

The scalp care compositions can further comprise a panthenol compound. As used herein, the term "panthenol compound" includes panthenol, one or more pantothenic acid derivatives, and mixtures thereof. Non-limiting examples of panthenol compounds include D-panthenol ([R]-2,4-dihydroxy-N-[3-hydroxypropyl)]-3,3-dimethylbutamide), D,L-panthenol, pantothenic acids and their salts (e.g., the calcium salt), panthenyl triacetate, royal jelly, panthetine, pantotheine, panthenyl ethyl ether, pangamic acid, pantoyl lactose, Vitamin B complex, or mixtures thereof. Accordingly, the scalp care composition may include from about 0.01% to about 5% of the panthenol compound, the scalp care composition may include from about 0.01% to 2.% of the panthenol compound, the scalp care composition may include from about 0.05% to about 2% of the panthenol compound; and the composition may include from about 0.1% to about 1% of the panthenol compound, for example, wherein the percentage is a weight percentage based on the total weight of the final hair care composition. The scalp care composition may further include about 0.15% of panthenol.

According to another aspect of the present invention, the scalp care compositions may be free of oleanolic acid and/or biotinyl-GHK, which is contrary to that described in U.S. Patent Application No. 20060067905.

Rheology Modifier

The scalp care composition may comprise a rheology modifier to improve various properties, such as increase the substantivity of the composition, improve the composition stability, non-dripping properties, sprayability and/or spreadability. Any suitable rheology modifier can be used. The scalp care composition may comprise from about 0.05% to about 10% of a rheology modifier, from about 0.1% to about 10% of a rheology modifier, from about 0.5% to about 2% of a rheology modifier, from about 0.7% to about 2% of a rheology modifier, from about 1% to about 1.5% of a rheology modifier. The rheology modifier may be a polyacrylamide thickener. The rheology modifier may be a polymeric rheology modifier. The polymeric rheology modifier may be a nonionic, water-soluble, cross-linked N-vinyl lactam homopolymers. N-vinyl lactam homopolymers can be selected from the group containing N-vinyl-2-pyrrolidone, N-vinyl-2-piperidone, N-vinyl-2-caprolactam, N-vinyl-3-methyl-2-pyrrolidone, N-vinyl-3-methyl-2-piperidone, N-vinyl-3-methyl-2-caprolactam, N-vinyl-4-methyl-2-pyrrolidone, N-vinyl-4-methyl-2-caprolactam, N-vinyl-5-methyl-2-pyrrolidone, N-vinyl-5-methyl-2-piperidone, N-vinyl-5,5-dimethyl-2-pyrrolidone, N-vinyl-3,3,5-trimethyl-2-pyrrolidone, N-vinyl-5-methyl-5-ethyl-2-pyrrololidone, N-vinyl-3,4,5-trimethyl-3-ethyl-2-pyrrolidone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl-7-methyl-2-caprolactam, N-vinyl-7-ethyl-2-caprolactam, N-vinyl-3,5-ethyl-2-caprolactam, N-vinyl-4,6-dimethyl-2-caprolactam, N-vinyl-3,5,7-trimethyl-2-caprolactam, and mixtures thereof. A nonlimiting example of a nonionic, water-soluble, cross-linked N-vinyl lactam homopolymer is a cross-linked N-vinyl-2-pyrrolidone homopolymer, sold under the tradename of Flexithix by Ashland Specialty Ingredients.

The scalp care composition may comprise additional rheology modifiers that are homopolymers that are nonionic or cationic based on acrylic acid, methacrylic acid or other related derivatives, non-limiting examples include polyacrylate, polymethacrylate, polyethylacrylate, and polyacrylamide.

The rheology modifiers may be alkali swellable and hydrophobically-modified alkali swellable acrylic copolymers or methacrylate copolymers non-limiting examples include acrylic acid/acrylonitrogens copolymer, acrylates/steareth-20 itaconate copolymer, acrylates/ceteth-20 itaconate copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylates/vinylneodecanoate crosspolymer, and acrylates/C10-C30 alkyl acrylate crosspolymer.

The additional rheology modifiers that are nonionic or cationic may be crosslinked acrylic polymers, a non-limiting example includes nonionic or cationic carbomers.

The additional rheology modifiers that are nonionic or cationic may be alginic acid based materials. Non-limiting examples include alginic acid propylene glycol esters.

The additional rheology modifier that are nonionic or cationic may be an associative polymeric thickeners. Non-limiting examples include hydrophobically modified cellulose derivatives, hydrophobically modified alkoxylated urethane polymers. Specific materials may include PEG-150/decyl alcohol/SMDI copolymer, PEG-150/stearyl alcohol/SMDI copolymer, and polyurethane-39. Other non-limiting examples include hydrophobically modified polyethers wherein these materials may have a hydrophobe that can be selected from cetyl, stearyl, oleayl, and combinations thereof, and a hydrophilic portion of repeating ethylene oxide groups with repeat units from 10-300, from 30-200, or from 40-150. Specific materials of this class include PEG-120-methylglucose dioleate, PEG-(40 or 60) sorbitan tetraoleate, PEG-150 pentaerythrityl tetrastearate, PEG-55 propylene glycol oleate, and PEG-150 distearate.

The additional rheology modifier that are nonionic or cationic may be cellulose and derivatives. Nonlimiting examples include microcrystalline cellulose, carboxymethylcelluloses, hydroxyethylcellulose, hydroxypropylcellulose, hydroxypropylmethylcellulose, methylcellulose, ethyl cellulose, nitro cellulose, cellulose powder, hydrophobically modified celluloses The rheology modifier that are nonionic or cationic may be a guar and guar derivatives. Non-limiting examples include hydroxypropyl guar, and hydroxypropyl guar hydroxypropyl trimonium chloride. The rheology modifier may be polyethylene oxide-polypropyne oxide copolymers. The rheology modifier may be polyvinylpyrrolidone, cross-linked polyvinylpyrrolidone and derivatives. The rheology modifier may be Polyvinylalcohol and derivatives. The rheology modifier may be polyethyleneimine and derivatives.

The additional rheology modifier that are nonionic or cationic may be silica. Non-limiting examples include fumed silica, precipitated silica, and silicone-surface treated silica.

The additional rheology modifier that are nonionic or cationic may be water-swellable clays. Non-limiting examples include laponite, bentolite, montmorilonite, smectite, and hectonite.

The additional rheology modifier that are nonionic or cationic may be gums. Non-limiting examples include guar gum, hydroxypropyl guar gum, Arabia gum, tragacanth, galactan, carob gum, karaya gum, and locust bean gum.

The additional rheology modifier that are nonionic or cationic may be dibenzylidene sorbitol, karaggenan, pectin, agar, quince seed (*Cydonia oblonga* Mill), starch (from rice, corn, potato, wheat, etc), starch-derivatives (e.g. carboxymethyl starch, methylhydroxypropyl starch), algae extracts, dextran, succinoglucan, and pulleran, Non-limiting examples of rheology modifiers that are nonionic or cationic include acrylates copolymer; acrylates/beheneth-25 methacrylate copolymer, acrylates/C10-C30 alkyl acrylate crosspolymer, acrylates/steareth-20 itaconate copolymer, ammonium polyacrylate/Isohexadecane/PEG-40 castor oil, C12-16 alkyl PEG-2 hydroxypropylhydroxyethyl ethylcellulose (HM-EHEC), carbomer, crosslinked polyvinylpyrrolidone (PVP), dibenzylidene sorbitol, hydroxyethyl ethylcellulose (EHEC), hydroxypropyl methylcellulose (HPMC), hydroxypropyl methylcellulose (HPMC), hydroxypropylcellulose (HPC), methylcellulose (MC), methylhydroxyethyl cellulose (MEHEC), PEG-150/decyl alcohol/SMDI copolymer, PEG-150/stearyl alcohol/SMDI copolymer, polyacrylamide/C13-14 isoparaffin/laureth-7, polyacrylate 13/polyisobutene/polysorbate 20, polyacrylate crosspolymer-6, polyamide-3, polyquaternium-37 (and) hydrogenated polydecene (and) trideceth-6, polyurethane-39, and crosspolymer (and) isohexadecane (and) polysorbate 60. Exemplary commercially-available rheology modifiers include Klucel M CS, Klucel H CS, Klucel G CS, Benecel E10M, Benecel K35M, and combinations thereof.

Carrier

According to another aspect of the present invention, the scalp care compositions may further include at least about 20 weight percent of an aqueous carrier. The aqueous carrier may be prepared from demineralized or distilled water, for example. The aqueous carrier comprises water or a combination of water with organic solvents (miscible or non-miscible with water) or silicone solvents. A volatile carrier may include water or a mixture of water and organic solvents. The solvents may be dermatologically acceptable. The carrier may comprise water with minimal or no significant concentrations of organic solvent, except as otherwise incidentally incorporated into the composition as minor ingredients of other components. Water, organic and silicone solvents that have boiling points below or equal to 250° C. are volatile solvents and volatile carriers. Volatile Solvents may have a boing point below or equal to 90° C., non-limiting examples include ethanol. Solvents with boiling points above 250° C. are considered non-volatile. In the present invention, the aqueous carrier may be present from about 1% to about 99%; from about 10% to about 75%; and from about 20% to about 50%. In the present invention, the composition may have from about 1% to about 99% of a volatile carrier wherein less than about 10% is a volatile solvent.

Non-limiting examples of a carrier may include water and water solutions of lower alkyl alcohols and polyhydric alcohol, the lower alkyl alcohols such as monohydric alcohols having 1 to 6 carbons, in one aspect, ethanol and isopropanol, and polyhydric alcohols such as glycols, glycerin and other diols.

Other acceptable carriers that may be used in the aqueous carrier include, but are not limited to alcohol compounds, such as ethanol. The composition may comprise alcohol, dipropylene glycol, and/or water.

The scalp care compositions may have a pH ranging from about 3.0 to about 10, which may be measured by taking a direct pH measurement using a standard hydrogen electrode of the composition at 25° C. Accordingly, the pH of the hair care composition may be within the range from about 4 to about 9, as a non-limiting example.

Scalp Health Agent

Scalp Health agents may be surfactant soluble or particulates. Surfactant soluble scalp health agent may be one material or a mixture selected from the groups consisting of: azoles, such as climbazole, ketoconazole, itraconazole, econazole, and elubiol; hydroxy pyridones, such as octopirox (piroctone olamine), ciclopirox, rilopirox, and MEA-Hydroxyoctyloxypyridinone; kerolytic agents, such as salicylic acid and other hydroxy acids; strobilurins such as azoxystrobin and metal chelators such as 1,10-phenanthroline.

The present invention may contain azole anti-microbials which may be an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. The azole anti-microbial agent may be ketoconazole.

The compositions of the present invention may also contain a scalp health agent particulates. Suitable, non-limiting examples of scalp health agent particulates include: pyridinethione salts, selenium sulfide, particulate sulfur, and mixtures thereof. Such scalp health agent particulate should be physically and chemically compatible with the essential components of the composition, and should not otherwise unduly impair product stability, aesthetics or performance.

1. Pyridinethione Salts

Pyridinethione scalp health agent particulates, especially 1-hydroxy-2-pyridinethione salts, may be a particulate scalp health agent for use in compositions of the present invention. The concentration of pyridinethione scalp health agent particulate typically ranges from about 0.1% to about 10%, by weight of the composition. The present invention may contain pyridinethione salts including those formed from heavy metals such as zinc, copper, tin, cadmium, magnesium, aluminum and zirconium. The pyridinethione salt may be formed from a heavy metal zinc, and further, the zinc salt of 1-hydroxy-2-pyridinethione (known as "zinc pyridinethione" or "ZPT"), and yet a further of 1-hydroxy-2-pyridinethione salts in platelet particle form, wherein the particles have an average size of up to about 20μ. The particles may have an average size up to about 5μ, and may be up to about 2.5μ. Salts formed from other cations, such as sodium, may also be suitable. Pyridinethione anti-dandruff agents are described, for example, in U.S. Pat. Nos. 2,809,971; 3,236,733; 3,753,196; 3,761,418; 4,345,080; 4,323,683; 4,379,753; and 4,470,982. It is contemplated that when ZPT is used as the scalp health agent particulate in the compositions herein, that the growth or re-growth of hair may be stimulated or regulated, or both, or that hair loss may be reduced or inhibited, or that hair may appear thicker or fuller.

2. Other Anti-Microbial Actives

In addition to the scalp health agent selected from polyvalent metal salts of pyrithione, the present invention may further comprise one or more anti-fungal or anti-microbial actives in addition to the metal pyrithione salt actives. Suitable anti-microbial actives include coal tar, sulfur, whitfield's ointment, castellani's paint, aluminum chloride, gentian violet, octopirox (Piroctone olamine), ciclopirox olamine, undecylenic acid and it's metal salts, potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. The present invention may include anti-microbials including itraconazole, ketoconazole, selenium sulphide and coal tar.

b. Selenium Sulfide

Selenium sulfide is a particulate scalp health agent suitable for use in the anti-microbial compositions of the present invention. Selenium sulfide is generally regarded as a compound having one mole of selenium and two moles of sulfur, although it may also be a cyclic structure that conforms to the general formula $Se_xS_y$, wherein x+y=8. Average particle diameters for the selenium sulfide are typically less than 15 μm, as measured by forward laser light scattering device (e.g. Malvern 3600 instrument), and less than 10 μm.

Selenium sulfide compounds are described, for example, in U.S. Pat. Nos. 2,694,668; 3,152,046; 4,089,945; and 4,885,107.

c. Sulfur

Sulfur may also be used as a particulate anti-microbial/scalp health agent in the anti-microbial compositions of the present invention.

d. Keratolytic Agents

The present invention may further comprise one or more keratolytic agents such as Salicylic Acid.

The present invention may also comprise a combination of surfactant soluble anti-scalp health agents and particulate scalp health agents. The present invention may contain the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

e. Additional Anti-Microbial Actives

Additional anti-microbial actives of the present invention may include extracts of melaleuca (tea tree) and charcoal. The present invention may also comprise combinations of anti-microbial actives. Such combinations may include octopirox and zinc pyrithione combinations, pine tar and sulfur combinations, salicylic acid and zinc pyrithione combinations, octopirox and climbazole combinations, and salicylic acid and octopirox combinations, zinc pyrithione and climbazole and mixtures thereof.

The scalp health agent may be present in an amount from about 0.01% to 10%; from about 0.1% to 9%; from about 0.25% to 8%; from about 0.5% to 6%.

The present invention may further contain an effective amount of an insoluble zinc salt. Nonlimiting examples of insoluble zinc salts are zinc oxalate, zinc tannate, zinc tartrate, zinc citrate, zinc oxide, basic zinc carbonate, zinc hydroxide, zinc oleate, zinc phosphate, zinc silicate, zinc stearate, zinc sulfide, zinc undecylate and mixtures thereof. In the present invention, the composition may comprise from about 0.001% to about 10%, or from about 0.01% to about 7%, or from about 0.1% to about 5% of an insoluble zinc salt, by total weight of the composition The present invention may further comprise an effective amount of a zinc-containing layered material. Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. The ZLM may be selected from the group consisting of: hydrozincite (zinc carbonate hydroxide), basic zinc carbonate, aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. The ZLM may be a layered double hydroxide conforming to the formula $[M^{2+}_{1-x}M^{3+}_{x}(OH)_2]^{x+}A^{m-}_{x/m}\cdot nH_2O$ wherein some or all of the divalent ions ($M^{2+}$) are zinc ions (Crepaldi, E L, Pava, P C, Tronto, J, Valim, J B *J. Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999, 38, 4211-6). In the present invention the ZLM may be a hydroxy double salt conforming to the formula $[M^{2+}_{1-x}M^{2+}_{1+x}(OH)_{3(1-y)}]^+$ $A^{n-}_{(1=3y)/n}\cdot nH_2O$ where the two metal ions ($M^{2+}$) may be the same or different. If they are the same and represented by zinc, the formula simplifies to $[Zn_{1+x}(OH)_2]^{2x+}2xA^-\cdot nH_2O$. This latter formula represents (where x=0.4) materials such as zinc hydroxychloride and zinc hydroxynitrate. The ZLM may be zinc hydroxychloride and/or zinc hydroxynitrate. These are related to hydrozincite as well wherein a divalent anion replace the monovalent anion. These materials can also be formed in situ in a composition or in or during a production process.

In the present invention, the composition may comprise basic zinc carbonate. Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA). Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

In the present invention, the composition may comprise an effective amount of a zinc-containing layered material. In the present invention, the composition may comprise from about 0.001% to about 10%, or from about 0.01% to about 7%, or from about 0.1% to about 5% of a zinc-containing layered material, by total weight of the composition.

In the present invention having a zinc-containing layered material and a pyrithione or polyvalent metal salt of pyrithione, the ratio of zinc-containing layered material to pyrithione or a polyvalent metal salt of pyrithione may be from about 5:100 to about 10:1, or from about 2:10 to about 5:1, or from about 1:2 to about 3:1.

Polyols

Polyols are a component of the present invention, with a nonlimiting example of a polyol being glycerin. Glycerin is a colorless, odorless, viscous liquid that is very common for use in personal care applications and pharmaceutical formulations. Glycerin contains three hydroxyl groups that are responsible for its solubility in water and its humectant nature. Glycerin is well known as hair and skin benefit agent in personal care applications. This material can penetrate into a human hair to provide conditioning and softness via plasticization of the hair fiber while maintaining a very clean surface feel. Glycerin has been observed to clean more hydrophobic soil components (i.e. sebum) than water.

The levels of glycerin range from about 0.1% to about 10%, from about 0.5% to about 8%, from about 1% to about 7% and from about 3.0% to about 6.0% by weight of the shampoo composition.

In the scalp care composition, other polyols may be used. Non-limiting examples include propylene glycol, sugar polyols such as sorbitol, aloe vera gel and honey.

Silicones

The conditioning agent of the compositions of the present invention can be a silicone conditioning agent. The silicone conditioning agent may comprise volatile silicone, non-volatile silicone, or combinations thereof. The concentration of the silicone conditioning agent typically ranges from about 0.01% to about 10%, by weight of the composition, from about 0.1% to about 8%, from about 0.1% to about 5%, and/or from about 0.2% to about 3%. Non-limiting examples of suitable silicone conditioning agents, and optional suspending agents for the silicone, are described in U.S. Reissue Pat. No. 34,584, U.S. Pat. Nos. 5,104,646, and 5,106,609, which descriptions are incorporated herein by reference. The silicone conditioning agents for use in the compositions of the present invention can have a viscosity, as measured at 25° C., from about 20 to about 2,000,000 centistokes ("cSt"), from about 1,000 to about 1,800,000 cSt, from about 50,000 to about 1,500,000 cSt, and/or from about 100,000 to about 1,500,000 cSt.

The dispersed silicone conditioning agent particles typically have a volume average particle diameter ranging from about 0.01 micrometers to about 50 micrometers. For small particle application to hair, the volume average particle diameters typically range from about 0.01 micrometer to about 4 micrometers, from about 0.01 micrometers to about 2 micrometers, from about 0.01 micrometer to about 0.5 micrometers. For larger particle application to hair, the volume average particle diameters typically range from about 5 micrometers to about 125 micrometers, from about 10 micrometers to about 90 micrometers, from about 15 micrometers to about 70 micrometers, and/or from about 20 micrometers to about 50 micrometers.

Additional material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), incorporated herein by reference.

Silicone emulsions suitable for use in the present invention and may include, but are not limited to, emulsions of insoluble polysiloxanes prepared in accordance with the descriptions provided in U.S. Pat. No. 4,476,282 and U.S. Patent Application Publication No. 2007/0276087. Accordingly, suitable insoluble polysiloxanes include polysiloxanes such as alpha, omega hydroxy-terminated polysiloxanes or alpha, omega alkoxy-terminated polysiloxanes having a molecular weight within the range from about 50,000 to about 500,000 g/mol. The insoluble polysiloxane can have an average molecular weight within the range from about 50,000 to about 500,000 g/mol. For example, the insoluble polysiloxane may have an average molecular weight within the range from about 60,000 to about 400,000; from about 75,000 to about 300,000; from about 100,000 to about 200,000; or the average molecular weight may be about 150,000 g/mol. The insoluble polysiloxane can have an average particle size within the range from about 30 nm to about 10 micronmeters. The average particle size may be within the range from about 40 nm to about 5 micrometers, from about 50 nm to about 1 micrometers, from about 75 nm to about 500 nm, or about 100 nm, for example.

The average molecular weight of the insoluble polysiloxane, the viscosity of the silicone emulsion, and the size of the particle comprising the insoluble polysiloxane are determined by methods commonly used by those skilled in the art, such as the methods disclosed in Smith, A. L. *The Analytical Chemistry of Silicones*, John Wiley & Sons, Inc.: New York, 1991. For example, the viscosity of the silicone emulsion can be measured at 30° C. with a Brookfield viscosimeter with spindle 6 at 2.5 rpm. The silicone emulsion may further include an additional emulsifier together with the anionic surfactant, Other classes of silicones suitable for use in compositions of the present invention include but are not limited to: i) silicone fluids, including but not limited to, silicone oils, which are flowable materials having viscosity less than about 1,000,000 cSt as measured at 25° C.; ii) aminosilicones, which contain at least one primary, secondary or tertiary amine; iii) cationic silicones, which contain at least one quaternary ammonium functional group; iv) silicone gums; which include materials having viscosity greater or equal to 1,000,000 cSt as measured at 25° C.; v) silicone resins, which include highly cross-linked polymeric siloxane systems; vi) high refractive index silicones, having refractive index of at least 1.46, and vii) mixtures thereof.

Organic Conditioning Materials

The conditioning agent of the shampoo compositions of the present invention may also comprise at least one organic conditioning material such as oil or wax, either alone or in combination with other conditioning agents, such as the silicones described above. The organic material can be non-polymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

Scalp Health Actives

In the scalp care composition, a scalp health active may be added to provide scalp benefits in addition to the anti-fungal/anti-dandruff efficacy provided by the scalp health agent. This group of materials is varied and provides a wide range of benefits including moisturization, barrier improvement, anti-fungal, and anti-oxidant, anti-itch, and sensates. Such skin health actives include but are not limited to: vitamin E and F, salicylic acid, glycols, glycolic acid, PCA, PEGs, erythritol, glycerin, lactates, hyaluronates, allantoin and other ureas, betaines, sorbitol, glutamates, xylitols, menthol, menthyl lactate, iso cyclomone, benzyl alcohol, and natural extracts/oils including peppermint, spearmint, argan, jojoba and aloe.

Optional Ingredients

The compositions of the present invention can also additionally comprise any suitable optional ingredients as desired. For example, the composition can optionally include other active or inactive ingredients.

The compositions may include other common hair ingredients such as minoxidil, silicones, glycerin, conditioning agents, and other suitable materials. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein. Examples of these ingredient classes include, but are not limited to: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, rheology modifiers, hair conditioning agents, and surfactants.

The formulations of the present invention may be present in typical hair care compositions. They may be in the form of solutions or dispersion. The composition of the present invention may be hair tonics, treatment, and styling products, and treatment products; and any other form that may be applied to the hair and further it may be applied to the scalp and/or hair and scalp.

II. RESULTS

Several polymers are tested in a simple scalp treatment chassis consisting of: water, 50% ethanol, 0.1% ZPT, 0.16% zinc carbonate, 0.45% piroctone olamine, 0.5% fragrances. The polymers are added at levels recommended by the manufacturers and represented different classes of materials that could be potentially chosen to work in our system. In all cases, when the materials are not compatible in the system, there is an obvious negative interaction or lack of viscosity build that eliminated them from further follow-up. Table 1 showing the screened materials is below.

TABLE 1

| Polymer | Trade Name | Manufacturer | Class | Usage Level | Result |
|---|---|---|---|---|---|
| Polyquaternium-4 | Celquat H-100 | AkzoNobel | Cationic Polymer | 2.00% | The material does not impart enough viscosity to the formula to suspend the zinc carbonate, which readily settled out after addition. |
| Dehydroxanthan Gum | Amaze XT | Nouryon | Anionic Polymer | 0.85% | Within 24 hours the structure of the product breaks down into a mix of gel phase and a thing, low viscosity liquid. |
| Polyacylam & C13-14 Isoparaffin | Sepigel 305 | Seppic | Anionic Polymer | 0.85% | Within 24 hours the structure of the product breaks down into a mix of gel phase and a thing, low viscosity liquid. |
| PEG-150/Decyl Alcohol/SMDI Copolymer | Aculyn 44 | Dow | Nonionic Polymer | 5.0% (as added) | The formulation does not thicken, most assuredly due to the lack of appropriate materials for the polymer to associate with. |
| Acrylic Acid/VP Crosspolymer | Ultrathix P100 | Ashland | Anionic Polymer | 1.00% | The sample does not thicken as expected once the zinc carbonate is added. |
| Cross-linked PVP | Flexithix | Ashland | Nonionic Polymer | 3.50% | The sample shows no sign of issues so work is continued with it to understand shelf stability over time. On accelerated stability over 3 months at 40 C. it demonstrates to be effective at keeping the zinc carbonate suspended while maintaining a usable viscosity profile. |

FORMULATIONS AND EXAMPLES

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the hair care composition.

| Component | 1 | 2 | 3 | 4 |
|---|---|---|---|---|
| Water | 62.84 | 41.05 | 94.79 | 94.60 |
| Ethanol[1] | 30.00 | 50.00 | 0.00 | 0.00 |
| 2-Pyrrolidinone, 1-ethenyl-, homopolymer[2] | 3.50 | 4.00 | 2.00 | 2.00 |
| Polyacrylate-1 Crosspolymer[3] | 0.00 | 0.00 | 0.00 | 0.00 |
| Hydroxypropyl Methylcellulose[4] | 0.00 | 0.00 | 0.00 | 0.00 |
| Hydroxypropyl Starch Phosphate[5] | 0.00 | 0.00 | 0.00 | 0.00 |
| Zinc Pyrthione[6] | 0.10 | 0.00 | 0.00 | 0.10 |
| Zinc Carbonate[7] | 0.16 | 1.50 | 0.16 | 0.20 |
| Menthol[8] | 0.25 | 0.30 | 0.25 | 0.30 |
| Piroctone Olamine[9] | 0.45 | 0.45 | 0.10 | 0.10 |
| Hydrochloric Acid 6N[10] | QS | QS | QS | QS |
| Sodium Hydroxide[11] | QS | QS | QS | QS |
| Niacinamide[12] | 2.50 | 2.50 | 2.50 | 2.50 |
| Caffeine[13] | 0.10 | 0.10 | 0.10 | 0.10 |
| Panthenol[14] | 0.10 | 0.10 | 0.10 | 0.10 |
| PEG-40 Hydrogenated Castor Oil[15] | 0.00 | 0.00 | 1.00 | 1.00 |

-continued

| Component | 1 | 2 | 3 | 4 |
|---|---|---|---|---|
| Propylene Glycol[16] | 0.00 | 0.00 | 0.90 | 0.90 |
| Fragrance | 0.30 | 0.30 | 0.30 | 0.30 |

[1]SD-40B 200 Alcohol from Pride Solvents
[2]Flexithix from Ashland
[3]Aqua CC from Lubrizol
[4]Benecel K200M from Ashland
[5]Structure XL from AkzoNobel
[6]ZPT from Arch Chemical
[7]Zinc carbonate from the Bruggeman Group
[8]Menthol from Kerry Ingredients and Flavors
[9]Octopirox from Clariant
[10]HCl 6N Volumetric Solution from J T Baker
[11]Caustic Sode 50% from Univar
[12]Niacinamide from Lonza
[13]Caffieine from Merck
[14]D-Panthenol from BASF
[15]Cremophor RH-40 from BASF
[16]Propylene Glycol from Sigma Aldrich The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While the present invention has been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A scalp care composition comprising:
   a) from about 1% to about 99% by weight of the total scalp care composition, of an aqueous carrier;
   b) from about 0.05% to about 10% by weight of the total scalp care composition, of a nonionic, water-soluble, cross-linked N-vinyl lactam homopolymer;
   c) from about 0.001% to 10% by weight of the total scalp care composition, of an insoluble zinc salt.

2. The scalp care composition according to claim 1 wherein the insoluble zinc salt is selected from the group consisting of zinc oxalate, zinc tannate, zinc tartrate, zinc citrate, zinc oxide, basic zinc carbonate, zinc hydroxide, zinc oleate, zinc phosphate, zinc silicate, zinc stearate, zinc sulfide, zinc undecylate and mixtures thereof.

3. The scalp care composition according to claim 2 wherein the insoluble zinc salt is basic zinc carbonate.

4. The scalp care composition according to claim 1 wherein the scalp care composition further comprises from about 0.01% to 10% by weight of the total scalp care composition, of one or more scalp health agents.

5. The scalp care composition according to claim 4 wherein the scalp health agent is a particulate scalp benefit agent selected from the group consisting metal pyridinethione salts, selenium sulfide, particulate sulfur, and mixtures thereof.

6. The scalp care composition according to claim 5 wherein the particulate scalp benefit agent is zinc pyrithione.

7. The scalp care composition according to claim 4 wherein the scalp health agent is a surfactant soluble scalp health agent selected from the group consisting of azoles, hydroxy pyridones, ciclopirox, rilopirox, and MEA-hydroxyoctyloxypyridinone; kerolytic agents, strobilurins, metal chelators and combinations herein.

8. The scalp care composition according to claim 7 wherein the surfactant soluble scalp health agent is piroctone olamine.

9. The scalp care composition according to claim 1 wherein the aqueous carrier further comprises an organic solvent selected from the group consisting of dipropyleneglycol, propylene glycol, butylene glycol, 1,4-butanediol, 3-allyloxy-1,2-propanediol, dipropylene glycol n-butyl ether, 1,2-hexanediol, dimethyl isosorbide, ethanol, 1,3-butanediol, 1,3-propanediol, 2,2'-thiodiethanol, 1,6-hexanediol and combinations thereof.

10. The scalp care composition according to claim 9 wherein the aqueous carrier further comprises ethanol.

11. The scalp care composition according to claim 1 wherein the composition further comprises glycerin.

12. The scalp care composition according to claim 1 wherein the scalp care composition further comprises niacinamide in the range of 0.1% to 7.5% by weight of the total scalp care composition.

13. The scalp care composition according to claim 1 wherein the scalp care composition further comprises caffeine in the range of 0.01% to 3.0% by weight of the total scalp care composition.

14. The scalp care composition according to claim 1 wherein the scalp care composition further comprises panthenol in the range of 0.01% to 2.0% by weight of the total scalp care composition.

15. The scalp care composition according to claim 1 wherein the composition further comprises a silicone.

16. The scalp care composition according to claim 1 wherein the composition is a leave-on composition.

* * * * *